(12) United States Patent
Tamura et al.

(10) Patent No.: US 7,570,994 B2
(45) Date of Patent: Aug. 4, 2009

(54) APPARATUS AND METHOD FOR MAINTAINING A DEFIBRILLATOR BATTERY CHARGE AND OPTIONALLY COMMUNICATING

(75) Inventors: Paul S. Tamura, Seattle, WA (US); Daniel Yerkovich, Seattle, WA (US); Patrick F. Kelly, Edmonds, WA (US); Richard Nova, Kirkland, WA (US); Joseph Bradley Williamson, Mercer Island, WA (US); Stephen B. Johnson, Clinton, WA (US); Gary DeBardi, Kirkland, WA (US)

(73) Assignee: Medtronic Physio-Control Corp., Redmond, WA (US)

( * ) Notice: Subject to any disclaimer, the term of this patent is extended or adjusted under 35 U.S.C. 154(b) by 355 days.

(21) Appl. No.: 10/423,805

(22) Filed: Apr. 25, 2003

(65) Prior Publication Data
US 2004/0212344 A1 Oct. 28, 2004

(51) Int. Cl.
*A61N 1/39* (2006.01)
(52) U.S. Cl. ............................. 607/5; 607/33; 607/61; 320/111; 600/300
(58) Field of Classification Search .................. 607/5, 607/33, 61; 600/300; 320/111
See application file for complete search history.

(56) References Cited
U.S. PATENT DOCUMENTS

| | | | |
|---|---|---|---|
| 4,082,097 A | 4/1978 | Mann et al. ............ 128/419 PS |
| 4,590,943 A | 5/1986 | Paull et al. .................. 128/419 |
| 4,654,573 A | 3/1987 | Rough et al. ................... 320/2 |
| 5,224,870 A | 7/1993 | Weaver et al. ............... 439/157 |
| 5,536,979 A | 7/1996 | McEachern et al. ......... 307/104 |
| 5,575,807 A * | 11/1996 | Faller ............................. 607/5 |
| 5,630,836 A * | 5/1997 | Prem et al. ..................... 607/61 |
| 5,640,078 A | 6/1997 | Kou et al. ...................... 320/15 |
| 5,702,431 A * | 12/1997 | Wang et al. .................... 607/61 |
| 5,723,969 A | 3/1998 | Archer et al. .................. 320/2 |
| 5,741,305 A | 4/1998 | Vincent et al. ................. 607/5 |
| 5,773,961 A | 6/1998 | Cameron et al. ............ 320/132 |
| 5,991,665 A | 11/1999 | Wang et al. .................... 607/61 |
| 6,008,622 A | 12/1999 | Nakawatase ................ 320/108 |
| 6,016,046 A | 1/2000 | Kaite et al. ................. 320/108 |
| 6,035,235 A | 3/2000 | Perttu et al. .................... 607/5 |
| 6,072,299 A | 6/2000 | Kurle et al. ................. 320/112 |
| 6,127,063 A | 10/2000 | Kowalsky et al. ........... 429/100 |
| 6,137,261 A | 10/2000 | Kurle et al. ................. 320/132 |
| 6,198,253 B1 | 3/2001 | Kurle et al. ................. 320/132 |
| 6,456,883 B1 | 9/2002 | Torgerson et al. ............. 607/34 |

(Continued)

FOREIGN PATENT DOCUMENTS

WO    WO 01/97908    12/2001

*Primary Examiner*—Carl H Layno
*Assistant Examiner*—Deborah Malamud
(74) *Attorney, Agent, or Firm*—Shumaker & Sieffert, P.A.

(57) ABSTRACT

Defibrillator assemblies and methods to wirelessly transfer energy from an external source to a battery or other rechargeable power source within the defibrillator assembly. The transfer of energy may be through a non-contact interface on a defibrillator cradle or a docking station that mounts the defibrillator. The rate of energy transfer may be equal to the energy drain caused by self-discharge and automated self-testing. Accordingly, since the rate of energy transfer is lower than that required to run the defibrillator system continuously, several wireless methods of energy transfer may be used. In addition, the defibrillator assembly may communicate diagnostic and non-diagnostic data to the external source.

13 Claims, 8 Drawing Sheets

U.S. PATENT DOCUMENTS

| | | | |
|---|---|---|---|
| 6,524,240 B1 | 2/2003 | Thede | 600/300 |
| 6,928,322 B2 * | 8/2005 | Yerkovich et al. | 607/5 |
| 2003/0014090 A1 | 1/2003 | Abrahamson | 607/60 |
| 2003/0080712 A1 | 5/2003 | Tamura et al. | 320/103 |
| 2004/0078061 A1 | 4/2004 | Czgan et al. | 607/32 |

* cited by examiner

APPARATUS AND METHOD FOR MAINTAINING A DEFIBRILLATOR BATTERY CHARGE AND OPTIONALLY COMMUNICATING

TECHNICAL FIELD

The invention relates to medical devices, and in particular, to wirelessly charging a battery within a defibrillator.

BACKGROUND

Cardiac arrest is a life-threatening medical condition that may be treated with external defibrillation. External defibrillation includes applying electrodes to the patient's chest and delivering an electric shock to the patient to depolarize the patient's heart and restore normal sinus rhythm. The chance that a patient's heart can be successfully defibrillated increases significantly if a defibrillation pulse is applied quickly.

Until recently, only individuals such as paramedics, emergency medical technicians, police officers, and others trained in defibrillation techniques used defibrillators. However, in a cardiac arrest event the patient's need is urgent and the patient cannot wait for trained personnel to arrive. In recognition of the need for prompt treatment, automated external defibrillators (AEDs) are becoming more commonplace, and are available in venues such as health clubs, auditoriums, and most recently private homes. Ready availability of AEDs may mean that patients can get needed treatment promptly, and need not wait for emergency personnel to arrive. As a result, more lives may be saved.

An AED may be used infrequently, whether it is placed in a commercial setting or in a private household. The battery within the AED will gradually discharge because of self-discharge and automated self-testing that is conducted on a periodic basis (daily, weekly, etc.). Since the AED is used infrequently, the battery status may not be checked on a regular basis. As a result, when the AED is brought into use, possibly years after purchase, the battery may not have sufficient energy to allow the AED to perform its intended function (ECG analysis and defibrillation).

As part of ordinary maintenance procedures, AEDs deployed may be periodically checked. Typically in public venues a person, such as a security worker, may be assigned to make an inspection of each AED and confirm that the device is operational. The inspection may be relatively simple, because many AEDs perform one or more automatic self-diagnostic routines and provide one or more status indications that the device is operational or in need of service.

As part of the inspection, the responsible person regularly reviews each AED and checks its associated status indicators. The responsible person may also be required to prepare and maintain records showing that the inspections have been performed, as well as log the status and repair history of the AEDs. However, in a public venue having several AEDs, the cost of inspection may be significant. Further, a deployed AED may be unprepared to provide defibrillation therapy if the responsible person fails to make an inspection, forgets to make an inspection, or makes an inspection error.

These problems are exacerbated in a private venue or a household where an AED may be used even more infrequently, and thus the AED may have a larger chance of not being properly inspected. It may be more likely in a private venue or a household the user will forget about the AED due to the long time periods between AED uses. Thus, there is a greater chance in these private settings the AED battery will not be properly charged and that the user may not have purchased a replacement battery.

Generally, disposable batteries power most AEDs. There are presently AEDs, which have an option for using rechargeable batteries. In these AEDs, removing them from the unit and connecting an AC-powered charger charge the batteries. A problem associated with using these AEDs using AC power is that the leakage current to the patient must be kept below the limits set by industry standards, which require the use of large isolation components, typically transformers. These devices, while they have proved effective as AEDs, are also larger and heavier and thus make the AEDs more difficult to use and transport.

Another challenge with defibrillators is providing for user safety from the high voltages generated by the AED. In some AEDs, safety is provided by having no exposed, user-accessible contacts other than the defibrillation electrodes (pads). However, these AEDs utilize removable batteries that are inserted into the AED and removed when the battery is depleted. Having a traditional battery charger that is powered by the AC line power typically has user-accessible contacts that would have to be electrically isolated within the AED. This isolation would increase the cost and size of the AED.

SUMMARY

The invention overcomes the problems of the prior art. The invention provides medical device systems and methods to wirelessly transfer energy from an external source to a battery within the medical device. The invention transfers the energy through a non-contact interface through a cradle means or a docking station means. The rate of energy transfer is generally equal to the energy drain caused by self-discharge and automated self-testing. Accordingly, since the rate of energy transfer is lower than that required to run the medical device continuously, several wireless methods of energy transfer may be used. The present invention provides wireless energy transfer methods, such as inductively, capacitively, acoustically, optically, and electromagnetically transferring energy from an external source to a medical device. In addition, the invention may optionally provide the capability for the medical device to communicate diagnostic and non-diagnostic data to the external source.

DETAILED DESCRIPTION

Figure 1:
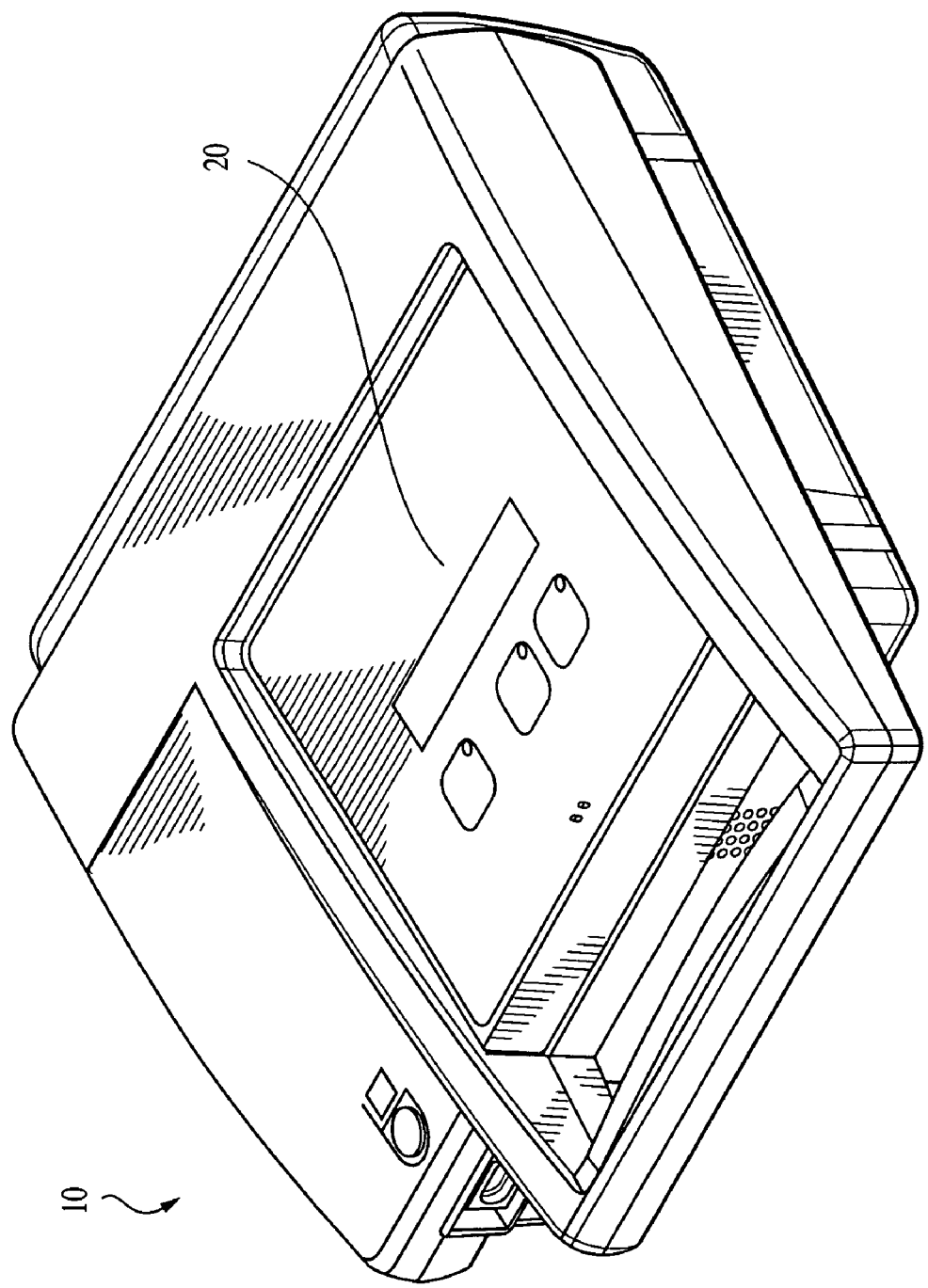
FIG. 1 is a perspective view of a portable defibrillator in accordance with the present invention.

The following detailed description is to be read with reference to the figures, in which like elements in different figures have like reference numerals. The figures, which are not necessarily to scale, depict selected embodiments and are not intended to limit the scope of the invention. Skilled artisans will recognize that the examples provided herein have many useful alternatives that fall within the scope of the invention.

The present invention is not limited to automatic external defibrillators and may be employed in many various types of electronic and mechanical devices for treating patient medical conditions such as external defibrillators, implantable defibrillators, pacemakers, cardioverter defibrillators, and neurostimulators. For purposes of illustration only, however, the present invention is below described in the context of automatic external defibrillators.

AED 10 is capable of administering defibrillation therapy to a patient. AED 10 includes an electrical source (not shown) that can generate one or more shocks to defibrillate the heart of a patient. The shocks may be delivered to the patient via two electrodes (not shown), which may be hand-held electrode paddles or adhesive electrode pads placed externally on the skin of the patient.

Figure 2:
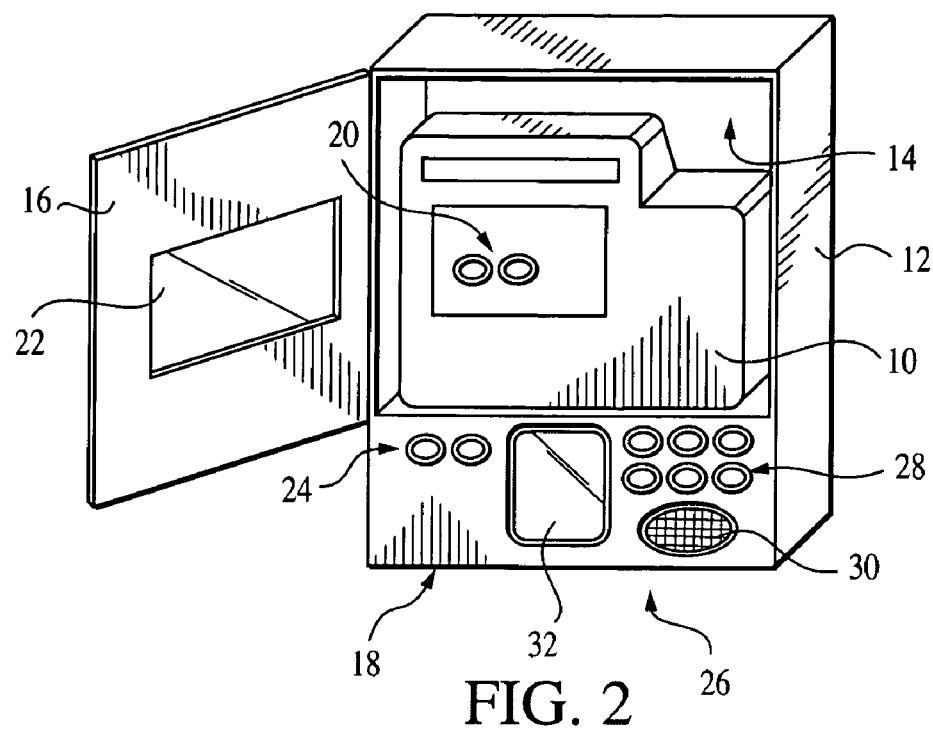
FIG. 2 is a perspective drawing of an automated external defibrillator in a cabinet docking station according to an embodiment of the invention.
Figure 3:
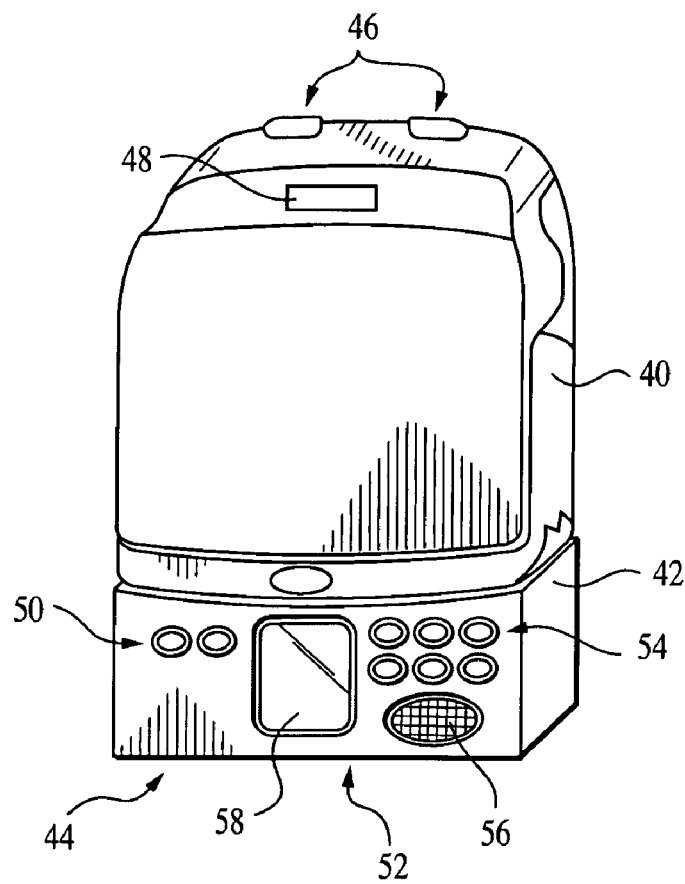
FIG. 3 is a perspective drawing of an automated external defibrillator in a bracket docking station according to another embodiment of the invention.

The electrodes may be packaged in a sealed pouch (not shown), such as an airtight foil bag, which protects the electrodes from the environment. The electrodes may include substances that may degrade or dry out when exposed to air. For example, the electrodes may include a hydrogel layer that hydrates the patient's skin, forms an interface with the patient, promotes adhesion of the electrodes to the skin and reduces the risk of burns. The electrodes may be stored in a pouch to prevent the hydrogel from drying out and losing its desirable properties. The pouch may be stowed inside AED 10 or inside cabinet 12 (FIG. 2 & FIG. 3).

An operator using AED 10 typically opens the pouch, retrieves the electrodes and places the electrodes in the correct positions on the patient's chest. In some models of AED 10, the operator may also couple the electrodes to AED 10 by plugging an electrical connector into a receptacle on AED 10.

Electrodes of the kind described above are intended for use on one occasion. Following use, the electrodes are discarded, and AED 10 may be supplied with a fresh pouch. Even if the electrodes are not used, however, the electrodes may have a shelf life. The pouch should be replaced when the shelf life expires.

Figure 4:
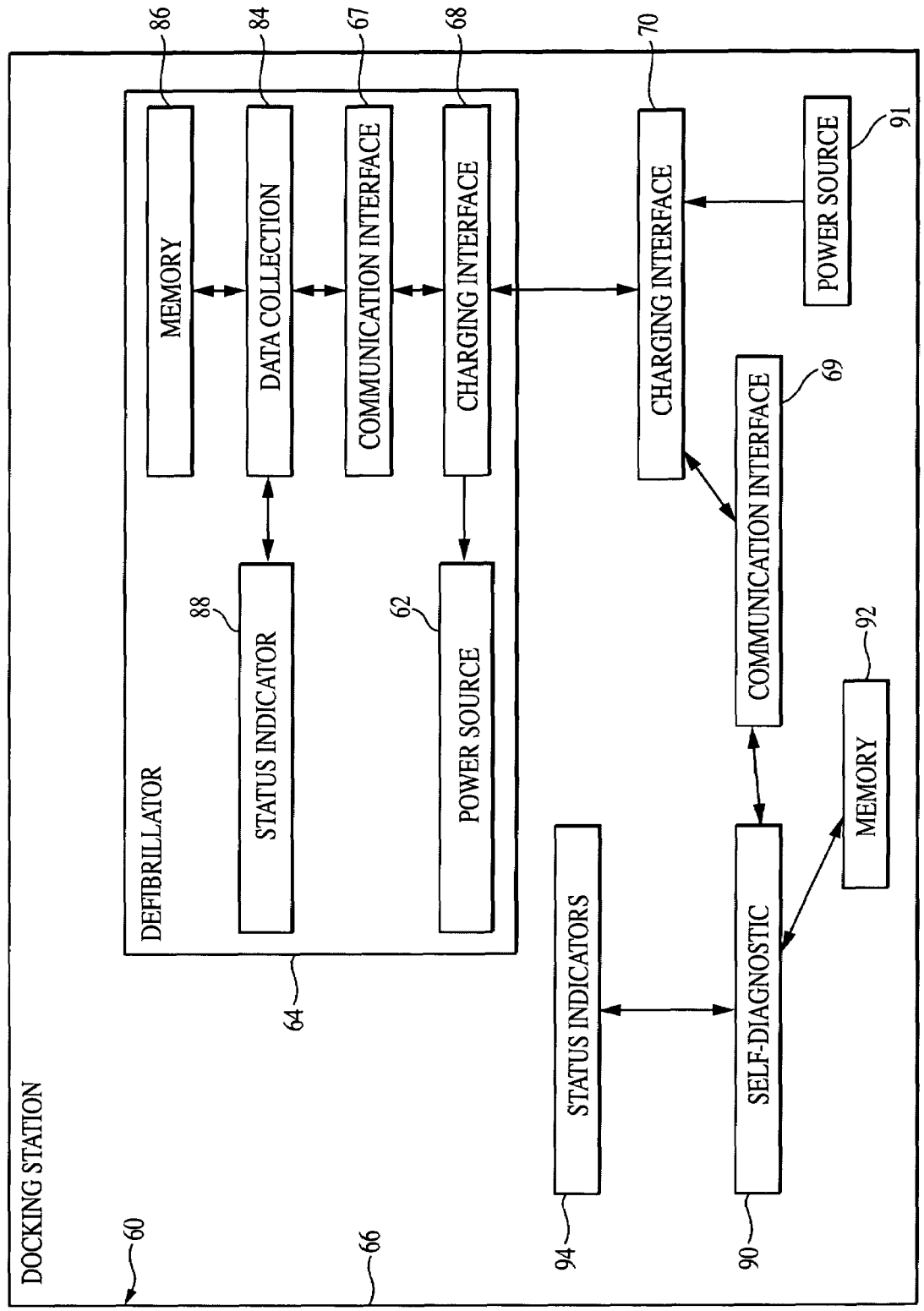
FIG. 4 is a block diagram illustrating a system for wirelessly charging an automated external defibrillator and optionally transmitting data from an automated external defibrillator, according to an embodiment of the invention.

AED 10 includes an internal power source 62 (FIG. 4). Power source 62 for many models of AED 10 is a battery. Battery power is advantageous in many respects. First, in many situations, the patient may be far from an electrical outlet. In those situations, AED 10 may rely upon a battery to supply the energy for the defibrillation shocks. Second, a power supply in the form of a battery makes AED 10 portable and useful in a wider variety of emergency situations.

AED 10 also comprises an energy storage device (not shown), such as one or more capacitors, and a charging circuit (not shown), such as a flyback charger. When a defibrillation shock is needed, the charging circuit transfers energy from the power supply to the energy storage device. When the energy stored in the energy storage device reaches a desired level, AED 10 is ready to deliver defibrillation therapy. The therapy may be delivered automatically or manually.

AED 10 may further include a microprocessor (not shown) that controls various functions of AED 10. The microprocessor may govern charging of the energy storage device, for example, or may evaluate heart rhythms of the patient sensed via the electrodes, or may deliver the defibrillation shocks automatically. The microprocessor may further execute a routine that performs a self-diagnostic test of AED 10 and acquire status information as a function of performing the self-diagnostic routine. The microprocessor may further acquire ECG data collected during a use of AED 10 on a patient and/or scene audio information recorded during use on a patient.

Status information pertains to the operating status of AED 10 and its attendant components. Status information may include, for example, data indicative of AED 10 being in good working order. Status information may also include data indicative of a fault or potential problem with AED 10, such as data indicative of a failed or damaged component. Data indicating that the battery is low, or that the battery is failing to hold a charge, are additional examples of AED status information. Status information may also include data indicating that the electrodes or other components are nearing the end of their shelf life, ECG data collected during use of AED 10 on a patient, and scene audio information recorded during use on a patient.

AED 10 may include one or more output elements 20 that convey status information to a person. As shown in FIG. 1, output elements 20 include visual annunciators, such as light-emitting diodes (LEDs) that illuminate or darken to convey status information. Output elements 20 may, for example, indicate whether AED 10 is in good working order, whether the battery is ready, or whether AED 10 needs service. Output elements 20 may include other or additional annunciators, such as a liquid crystal display (LCD), a cathode ray tube (CRT) display, a strobe, or a speaker that is capable of delivering an audible signal or a spoken message.

FIG. 2 is a perspective drawing of an automated external defibrillator (AED) 10 in an exemplary docking station 12. AED 10 and docking station 12 are illustrative of the practice of the invention, and for simplicity, the invention will be described in terms of AEDs and docking stations. The invention is not limited to docking stations and AEDs, however, but may include other devices, including a cradling device and other types of emergency medical devices.

In the example of FIG. 2, docking station 12 is a cabinet, comprising a compartment 14 that receives AED 10 and a hinged door 16 that closes to secure AED 10 inside compartment 14. AED 10 is portable. When an operator needs to use AED 10, the operator may open door 16 and lift AED 10 from compartment 14. Cabinet 12 also includes a base 18.

Hinged door 16 of cabinet 12 includes a window 22. When AED 10 rests in compartment 14 and door 16 is closed, output elements 20 may be visible through window 22. Base 18 of cabinet 12 also includes AED status output elements 24 that may be redundant of output elements 20 on AED 10. In other words, output elements 24 of cabinet 12 may convey the same status information as output elements 20 of AED 10. Output elements 24 may also convey AED status information in a different way than that conveyed by AED 10. Cabinet 12 may, for example, employ a simplified "OK—NOT OK" indicator system, while AED output elements 20 may be more specific about the nature of any problems.

The redundant presentation of status information may be advantageous in several respects. First, instead of facilitating observation of output elements 20 on AED 10, window 22 may impede observation of output elements 20. Because AED 10 may be recessed in compartment 14, for example, output elements 20 may not be visible through window 22 from all angles. Further, window 22 may be cracked or dirty or reflective of light sources that wash out the visual annunciators. Output elements 24 may also be larger or brighter than output elements 20, allowing the status information to be perceived from a greater distance or from a wider angle of view. Thus, a person wishing to perform a routine visual check on the status of AED 10 may obtain status information about AED 10 more readily.

Cabinet 12 presents status information via output elements 24 upon receiving the status information from AED 10. As will be described in more detail below, AED 10 may establish a communication link with cabinet 12, and may communicate status information to cabinet 12 wirelessly.

In addition to AED status output elements 24, base 18 includes docking station status output elements 26. Docking station status output elements 26 may include visual annunciators 28, a speaker 30 and a display screen 32. Visual annunciators 28 may comprise, for example, LEDs. Display screen 32 may comprise, for example, an LCD or CRT display.

Docking station status output elements 26 convey status information that is not redundant of status information conveyed by AED status output elements 24. The status information conveyed by docking station status output elements 26 may include status information pertaining to AED 10, or status information pertaining to cabinet 12. Further, as will be described below, AED 10, or cabinet 12, or both, may be connected to a network and the status information is conveyed to health care providers responsible for the care of a patient on which the AED was used or to service personnel responsible for maintaining the AED.

Visual annunciators 28 may convey, for example, that cabinet 12 is in good working order, or that the communication interfaces of cabinet 12 are working properly. Speaker 30 may convey, for example, an alarm signaling that door 16 is open or ajar, or verbal instructions concerning use of AED 10 or cabinet 12. Display screen 32 may convey any information in text or visual form, such as a pictorial instruction for opening door 16, or a text warning that AED 10 is out of service.

FIG. 3 is a perspective drawing of another AED 40 in a cradling station 42. In FIG. 3, cradling station 42 is a wall-mounted bracket, rather than a cabinet. Bracket 42 includes a shaped base 44 that receives AED 40 and supports AED 40. Bracket 42 also includes clasps 46, which, in cooperation with base 44, retain AED 40 and secure AED 40 to bracket 42. Clasps 46 may be flexible. When an operator needs to use AED 40, the operator may pull AED 40 from clasps 46 and lift AED 40 out of base 44.

AED 40 may include one or more output elements 48 that convey status information about AED 40, and base 44 may include AED status output elements 50 that may be redundant of output elements 48. As will be described in more detail below, AED 40 may establish a communication link with bracket 42. AED 40 may communicate status information to bracket 42, which bracket 42 may present via output elements 50 on base 44.

Output elements 48 and 50 may be similar to output elements 20 and 24 shown in FIG. 2. Although output elements 48 are not recessed in a compartment or obscured by a window, output elements 48 may be small or difficult to read at a distance. Output elements 50 may be more easily perceived from a greater distance or from a wider angle of view, allowing a person to readily obtain status information about AED 40.

Base 42 includes cradling station status output elements 52. Like docking station status output elements 26 shown in FIG. 2, cradling station status output elements 52 may include visual annunciators 54, a speaker 56 and a display screen 58.

The embodiments of an AED, docking station, and cradling station shown in FIGS. 1, 2, and 3 are for purposes of illustration. The invention is not limited to the arrangements depicted. For example, the invention encompasses embodiments in which the docking station output elements are positioned above the AED, or on multiple sides of the AED. The invention encompasses embodiments that include more or fewer output elements than are shown. The invention also encompasses embodiments that include docking elements to retain the AED other than clasps, shaped bases, cabinets, and doors. Docking elements may include clamps, lids, covers, trays, shelves, drawers, latches, and the like.

Figure 5:
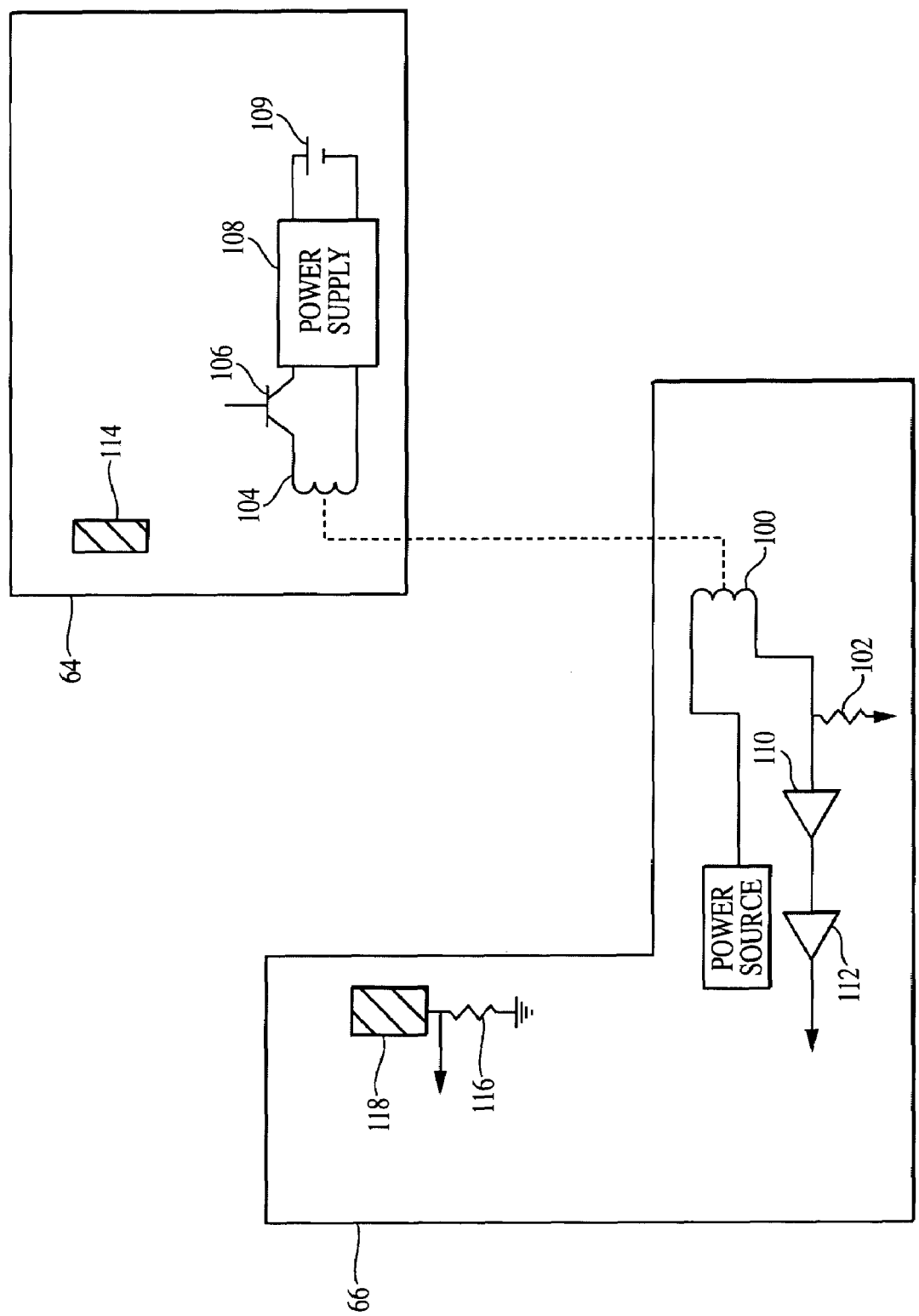
FIG. 5 is a schematic representation illustrating an embodiment for wirelessly charging an automated defibrillator, according to the present invention.

FIG. 4 is a block diagram illustrating an example defibrillator assembly 60 in which a docking station 66 wirelessly transfers energy from an external source to a battery 109 (FIG. 5). Assembly 60 may also optionally provide the capability for AED 64 to communicate diagnostic and non-diagnostic data to docking station 66. Assembly 60 provides an energy transfer rate (typically power) by at least an amount that offsets the power drain caused by self-discharge and periodic automatic testing of the AED in order to adequately maintain the charge of battery 109. Since this energy rate is lower than that required to continuously run AED 64, assembly 60 may transfer power between docking station 66 and AED 64 wirelessly without any user-accessible contacts. This lack of user accessible contacts maintains the integrity of assembly 60 and provides increased user isolation from high voltages generated by AED 64. In general, the present invention utilizes an electrostatic or electromagnetic field coupled between charging interface 70 in docking station 66 and charging interface 68 in AED 64 to wirelessly transfer energy. However, it is fully contemplated that other types of wireless techniques could be utilized to transfer energy, such as acoustically and optically without departing from the spirit of the present invention. Further, AED 64 and docking station 66 may be either of the embodiments depicted in FIGS. 1, 2, and 3, but are not limited to those embodiments. It is preferable that battery 109 is a rechargeable battery, however, it is fully contemplated battery 109 could include any type of power storage device such as a non-rechargeable battery or a large capacitor.

In a further aspect of the present invention, AED 64 wirelessly communicates with docking station 66 through communication interface 67 and communication interface 69, respectively. In particular, AED 64 includes a communication interface 67 that establishes a communication link with a communication interface 69 in docking station 66 through charging interface 68 and charging interface 70 respectively. The method of communication through charging interfaces 68 and 70 is discussed in more detail below.

Communication interface 69 may further be connected to a network. The network may comprise, for example, a public switched telephone network, a cellular telephone network, a local area network, a wide area network, a global computer network such as the Internet, an integrated services digital network, or the like. In some venues in which AED 64 and docking station 66 may be deployed, the venue may include a dedicated security network or a private building maintenance network. The network may include hard-wired electrical or optical communication links, wireless links, or a combination thereof. One method of communicating through a network is disclosed in U.S. patent application Ser. No. 10/378,001 filed Feb. 28, 2003 titled "Medical Device Status Information System", the entire content of which is incorporated herein by reference.

AED 64 includes a data collection module 84 that monitors the status of AED 64, collects ECG data during use of AED 64, and records scene audio information during AED 64 use on a patient. Data collection module 84 is a processor that executes one or more self-diagnostic routines. The self-diagnostic routines may be initiated by data collection module 84, or may be initiated in response to a change in the condition of AED 64, such as a component malfunction. By execution of a self-diagnostic routine, data collection module 84 performs one or more internal self-tests to acquire status information about the state of readiness of AED 64. Data collection module 84 may evaluate and identify matters that can be customer serviceable, such as battery or electrode replacement, and matters that may require a professional service call. AED 64 may record the status information, patient ECG data, and patient scene audio data in memory 86, and may transfer some or all of the data via communication interface 67 and charging interface 68. When the results of the self-tests indicate that AED 64 is "ready" for use, for example, status indicators 88 may provide a visible or audible indication of readiness. Status indicators 88 may comprise any of output elements 20 or 48 described in connection with FIGS. 2 and 3.

AED 64 may further communicate the collected data to docking station 66 via communication interfaces 67 and 69. Communication between AED 64 and docking station 66 may be made by a plurality of communication techniques through charging interfaces 68 and 70. In the embodiment shown in FIG. 4, AED 64 and docking station 66 may engage in two-way communication. The methods of data transfer are discussed in further detail below.

AED 64 and docking station 66 communicate via the wireless links provided by charging interfaces 68 and 70. These wireless links are implemented so that AED 64 may be quickly and easily removed from docking station 66 without hindrance. Communication between AED 64 and docking station 66 may also communicate via a physical communication link. When docking station 66 receives AED 64, mating acoustic or optical components in docking station 66 and AED 64 may engage, thereby enabling communication.

Docking station 66 includes a self-diagnostic module 90 that monitors the status of docking station 66. Self-diagnostic module 90 is a processor that executes a self-diagnostic routine to perform internal self-tests and to acquire status information about docking station 66. The self-diagnostic routines may be initiated by self-diagnostic module 90 or may be initiated in response to a change in the condition of docking station 66. Self-diagnostic module 90 may evaluate and identify matters that can be customer serviceable and matters that may require a professional service call.

In addition, self-diagnostic module 90 may collect, aggregate or interpret data received from AED 64. In some circumstances, self-diagnostic module 90 may use status information from AED 64 and from self-tests to pinpoint the source of a problem. Self-diagnostic module 90 may record the status information in memory 92, and may present some or all of the status information via one or more status indicators 94. Status indicators 94 may include AED status output elements, such as AED status output elements 24 and 50 in FIGS. 2 and 3, which convey AED status information redundantly. Status indicators 94 may also include output elements such as docking station status output elements 26 and 52 in FIGS. 2 and 3.

Status indicators 94 may convey status information pertaining to AED 64, status information pertaining to docking station 66.

Docking station 66 further includes a power source 91. Unlike AED 64, which is portable and is usually battery-powered, docking station 66 typically is stationary and may be line-powered. The invention is not limited to a line-powered docking station, however, but includes a docking station having a power source such as batteries or solar cells.

With reference to FIG. 5, showing a schematic representation illustrating an embodiment for wirelessly charging an automated defibrillator, the present invention utilizes an electromagnetic or electrostatic field coupled between docking station 66 and AED 64 to transfer energy wirelessly. In the embodiment of FIG. 5, the energy is coupled inductively. While docking station 66 is preferably connected to AC line power, this embodiment preferably does not use line frequency to transfer the energy. This is to avoid large inductors and relatively low rates of data transfer during communications between docking station 66 and AED 64. Preferably, the energy is modulated at a higher frequency, which allows for smaller magnetic components and quicker transfer of data during communications. For example, at 600 KHz the magnetic components can be extremely small and allow for a data transfer of 10,000 times faster than that of line power.

Charging interfaces 68 and 70 may comprise an internal and external charging circuit respectively. Charging interfaces 68 and 70 may provide inductive coupling accomplished by applying an AC signal at docking station 66 through inductor 100 and resistor 102, creating magnetic fields about inductor 100. When AED 64 is docked to docking station 66, the magnetic field is coupled into inductor 104, which produces a corresponding current. When AED 64 indicates that all tests have passed and AED 64 is ready for use, transistor 106 allows current to pass through to battery 109. This allows AED 64 to recharge.

Figure 6:
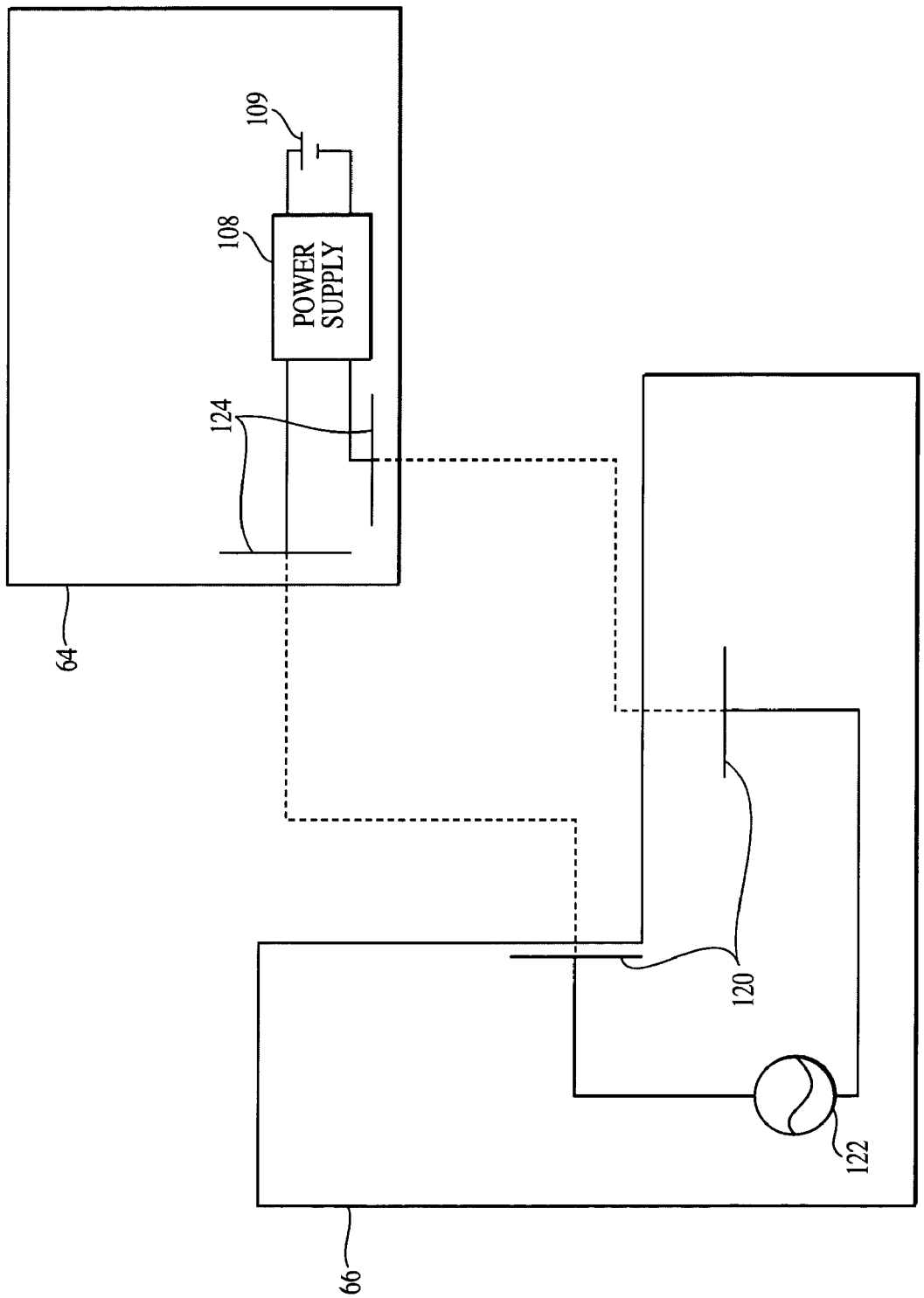
FIG. 6 is a schematic representation illustrating another embodiment for wirelessly charging an automated defibrillator, according to the present invention.

With reference to FIG. 6, showing a schematic representation illustrating another embodiment for wirelessly charging an automated defibrillator, the energy could be coupled capacitively. Once again, charging interfaces 68 and 70 may comprise an internal and external charging circuit respectively. In these circuits, proper alignment of a first pair of plates 120 connected to a power source 122 within docking station 66 and a second pair of plates 124 within AED 64 provides for capacitive coupling. Alternatively, the defibrillation electrodes, if connected to AED 64, could be used as the second pair of plates. Another embodiment includes acoustically coupling docking station 66 to AED 64, preferably at a frequency outside of the audible range. Another embodiment includes optically coupling docking station 66 and AED 64 using a light source illuminating photovoltaic cells mounted on AED 64.

As stated above, the embodiment to transfer energy discussed above may be combined with methods for transferring data between AED 64 and docking station 66 through modulation of the energy. The data could be stored by docking station 66 in a removable memory medium such as a floppy disk or flash memory card, or it could be transmitted to a receiving station through a telephone line or cellular telephone link or a network.

With reference to FIG. 5, one embodiment may be to utilize resistor 102 to set both the current flowing through inductor 100 and to create a voltage sensed by integrator 110 and a comparator 112. Integrator 110 and comparator 112 may be operational amplifiers configured to implement the integration and comparing function respectively. When AED 64 is not present at docking station 66, a specific voltage drop will be detected across resistor 102 and integrator 110. If AED 64 is docked in docking station 66 and is receiving current from inductor 104, the voltage detected across resistor 102 and integrator 110 will be lower since AED 64 presents a load to the circuit. Thus, a simple piece of data, the presence or absence of AED 64 is transmitted.

In another embodiment, AED 64 can alert the user of the need for refurbishment of AED 64 after it has been used on a patient. If AED 64 determines it is not "ready" (e.g., it has been used and needs refurbishing or has failed a self test), then data collection module 84 will turn off transistor 106 to block current flow. This transmits additional data, however, docking station 66 cannot distinguish between the absence of AED 64 or when AED 64 is not "ready". Therefore, AED 64 is fitted with magnet 114, which produces a magnetic field. At docking station 66 voltage is applied to resistor 116, which is connected to a hall-effect switch 118. It is noted that switch 118 could also be a reed switch or any other magnetic sensor without departing from the spirit of the invention. If AED 64 is docked to docking station 66, hall effect switch 118 detects the magnetic field produced by magnet 114 and produces a signal. This signal may be used to instruct docking station 66 to begin interfacing with AED 64. Additionally, the signal may be utilized in conjunction with comparator 112 to distinguish from a no-load situation when AED 64 is not docked and a no-load situation when AED 64 is docked, but not ready to interface. Alternatively, magnet 114 could be used to activate hall effect switch 118 wired to a conventional alarm monitoring system such that the alarm monitoring service would be alerted to the removal of AED 64 from docking station 66.

In another embodiment, AED 64 may provide different current loads to docking station 66 based on varying AED status. The resulting voltages are sensed by docking station 66 with distinct voltages equating to different device information (e.g., battery low, service requested, etc.). In this embodiment, a variable load device would be included on AED 64 and by replacing comparator 112 with an analog-digital converter or incorporating multiple comparators. These different current loads could be used to distinguish between the absence of AED 64, the presence of AED 64 that has been used on a patient, the presence of an AED 64 that has failed a self test, or other useful information. The number of levels of current that can be reliably distinguished limits the number of different status messages.

In another embodiment, AED 64 could vary the load on a cycle-by-cycle basis to transmit digital information, one bit per cycle. Alternately in another embodiment, AED 64 could modulate the load at a frequency higher than that used to transmit the power. This carrier frequency could be frequency modulated, phase modulated, or amplitude modulated to transmit digital information.

Figure 7:
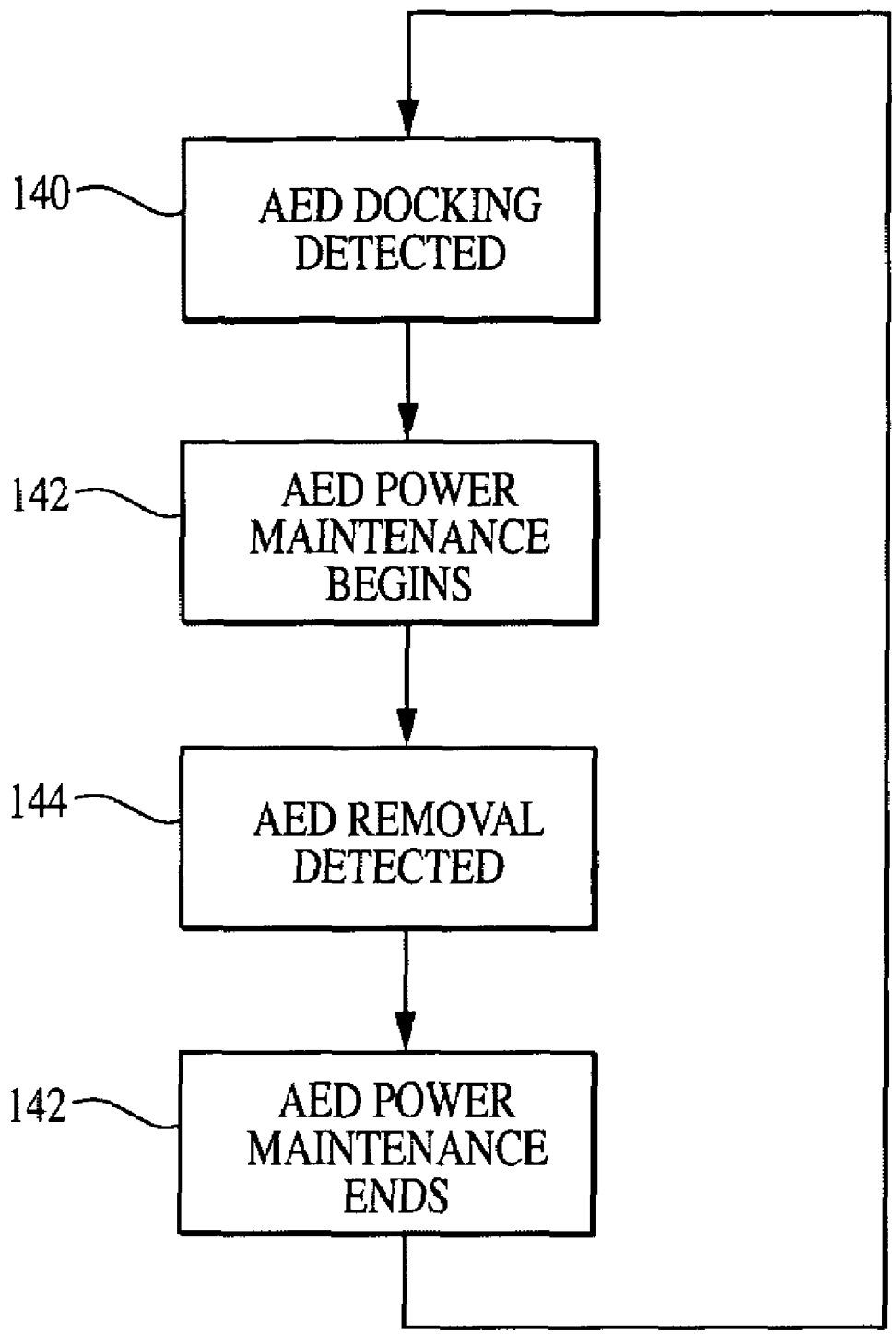
FIG. 7 is a flow diagram illustrating a technique for wirelessly charging a medical device such as an AED according to an embodiment of the invention.

With reference to FIG. 7, a flow diagram illustrating a technique for wirelessly charging a medical device such as an AED is shown. At state 140, docking station 66 has detected AED 64 has been docked and is in physical contact with docking station 66. This can happen in a variety of methods some of which are discussed above, such as hall effect switch 118 detecting a magnetic field produced by magnet 114 and producing a signal used to instruct docking station 66 to begin interfacing with AED 64. However, other types of detection methods are fully contemplated, such as optical detection, user input at the docking station indicating whether AED 64 is docked, and using a proximity sensor, without departing from the spirit of the invention. Once AED 64 is detected as being docked then docking station 66 begins transferring energy to AED 64 as shown in state 142. As mentioned already the energy transfer can occur using many methods such as inductive, capacitive, acoustic, optical, and electromagnetic. As stated, the energy rate of transfer (typically power) is generally equal to or greater than the drain to battery 109 caused by self discharge and periodic automatic testing to maintain the charge of battery 109. Therefore, if AED 64 remains docked for a long period of time, the energy rate of transfer will eventually charge battery 109. At state 144 docking station 66 detects that AED 64 has been removed. For example, AED 64 is needed for use on a patient. When AED 64 is detected as removed, docking station 66 stops transferring energy as shown at state 146. The process then begins again when it is detected that AED is docked at docking station 66 shown at state 140.

Figure 8:
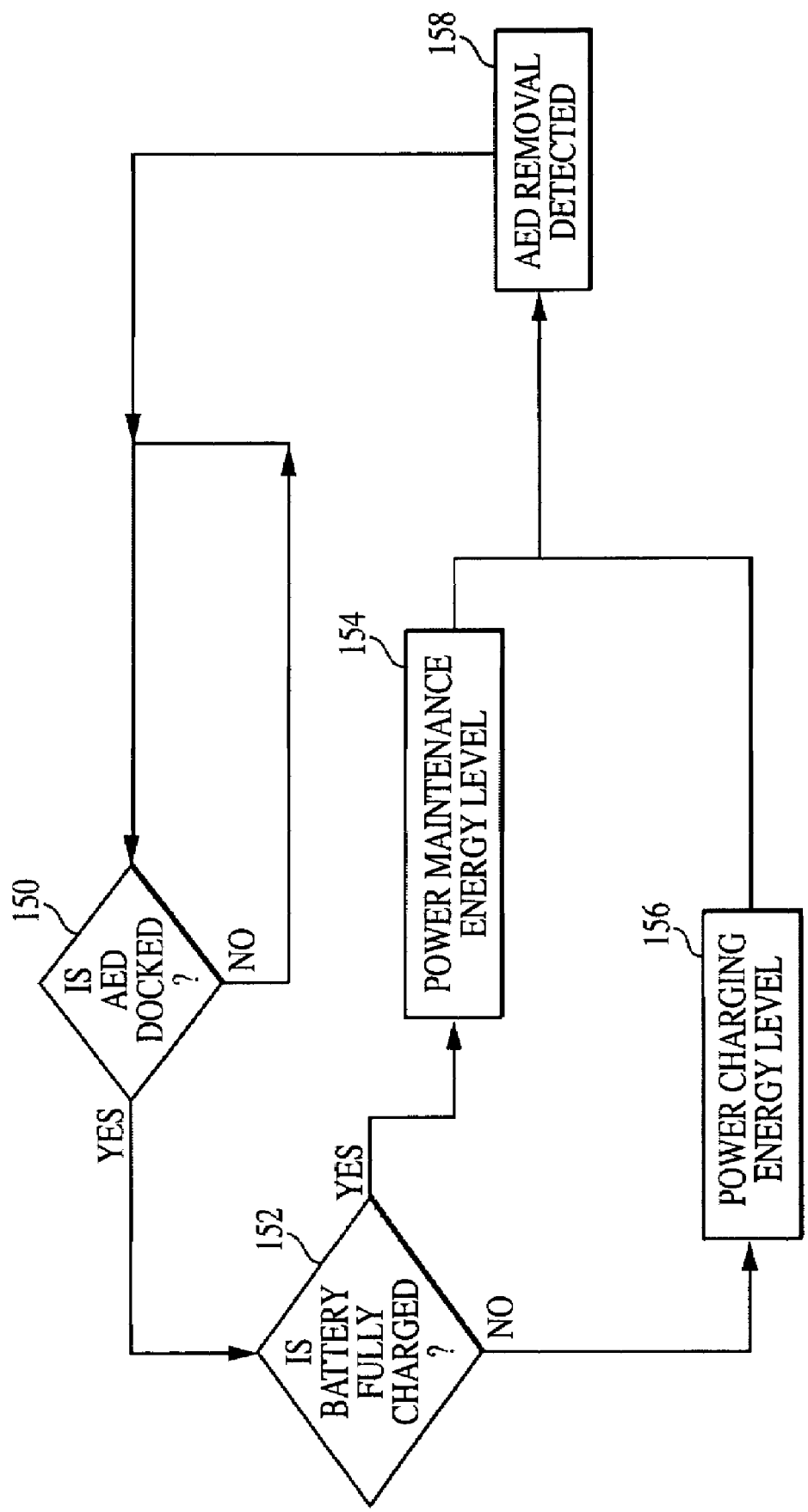
FIG. 8 is a flow diagram illustrating a technique for wirelessly charging a medical device such as an AED according to another embodiment of the invention.

With reference to FIG. 8, a flow diagram illustrating another embodiment for wirelessly charging a medical device such as an AED is shown. Similar to state 140, state 150 detects when AED 64 is docked in docking station 66. In contrast to the embodiment of FIG. 7, when AED 64 is docked, it begins to communicate to docking station 66 whether battery 109 is fully charged or not at state 152. AED 64 can communicate this status in any of the methods discussed above. If battery 109 is fully charged or charged to within 90% of capacity, then docking station 66 will transfer energy at a level that maintains the battery consumption of AED 64 at state 154. If battery 109 is not fully charged or below a charge of 90%, then docking station 66 will transfer energy at a rate slightly above a level that would maintain the battery consumption of AED 64 at state 156. This allows for enough energy to slowly charge battery 109. This charging capacity is more than adequate for an AED that is used infrequently. If AED 64 is removed from docking state 66, then any energy transfer from docking station 66 is stopped as shown at state 158. This process then begins again when AED 64 is placed back in docking station 66 as shown at state 150.

Figure 9:
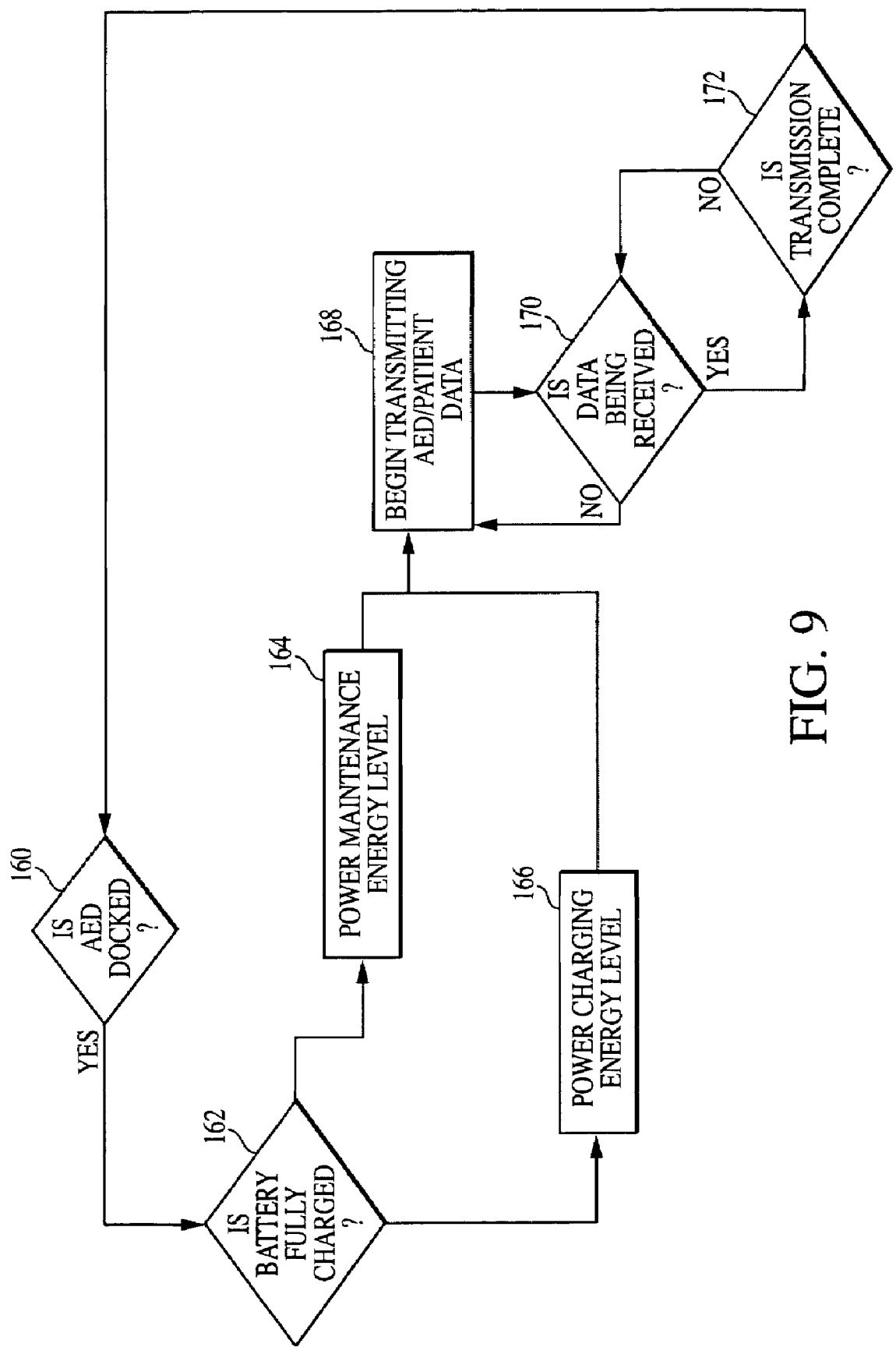
FIG. 9 is a flow diagram illustrating a technique for wirelessly charging and communicating with a medical device such as an AED according to an embodiment of the invention.

With reference to FIG. 9, a flow diagram illustrating another embodiment for wirelessly charging a medical device such as an AED is shown. Similar to state 140 and 150, state 160 detects when AED 64 is docked in docking station 66. When AED 64 is docked, it begins to communicate to docking station 66 whether battery 109 is fully charged or not at state 162. AED 64 can communicate this status in any of the methods discussed above. If battery 109 is fully charged or charged to within 90% of capacity, then docking station 66 will transfer energy at a level that maintains the battery power consumption of AED 64 at state 164. If battery 109 is not fully charged or below a charge of 90%, then docking station 66 will transfer energy at a rate slightly above a level that would maintain the battery power consumption of AED 64 at state 166. Regardless of which energy rate is chosen AED 64 begins to transmit AED status data and patient ECG and scene audio data to docking station 66 using any of the methods discussed above at state 168. Docking station 66 then determines whether it is receiving the data at state 170. If no data is being received, docking station 66 interrogates AED 64 and instructs it to start sending the data. If data is being received, docking station 66 then waits for data indicating that the data transmission is complete at state 172. If the transmission is complete and AED 64 is still docked, then docking station 66 continues to transfer energy at the desired rate. If the transmission is not complete and AED 64 is still docked, then docking station 66 continues to monitor whether the data is being received at state 170. If AED 64 is removed from docking station 66 at any moment in the present embodiment, the power and data transfer is interrupted and the process returns to state 160.

One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A defibrillator assembly comprising:
a defibrillator housing;
a rechargeable power source carried in the housing that selectively sources power used for a defibrillation shock, wherein the rechargeable power source is coupled to a recharging interface circuit carried in the housing, and wherein the recharging interface circuit wirelessly receives energy to charge the rechargeable power source;
a docking station;
an external charging circuit located outside of the housing and within the docking station, wherein the external charging circuit wirelessly transfers energy to the power source via a wireless coupling from the external charging circuit to the recharging interface circuit without conductive electrical contact between the docking station and the recharging interface circuit, and wherein the docking station supports the housing while the external charging circuit wirelessly transfers energy to the power source; and
communication means to transmit and receive defibrillator information between the housing and the docking station.

2. The defibrillator assembly of claim 1, wherein the communication means includes the external charging circuit.

3. The defibrillator assembly of claim 1, wherein the defibrillator information is wirelessly transferred between the housing and the docking station.

4. The defibrillator assembly of claim 1, wherein the defibrillator information includes at least one of defibrillator status, patient ECG data, scene audio information recorded during use of the defibrillator housing, or diagnostic data.

5. The defibrillator assembly of claim 1, wherein the recharging interface circuit modulates the transfer of energy, the modulation occurring in patterns that represent defibrillator information from within the housing.

6. The defibrillator assembly of claim 5, wherein the external charging circuit receives the defibrillator information from within the housing from the modulation of the transfer of energy.

7. The defibrillator assembly of claim 1, wherein the external charging circuit transfers energy to the recharging interface circuit inductively.

8. The defibrillator assembly of claim 1, wherein the external charging circuit transfers energy to the recharging interface circuit capacitively.

9. The defibrillator assembly of claim 1, wherein the external charging circuit transfers energy to the recharging interface circuit optically.

10. The defibrillator assembly of claim 1, wherein the external charging circuit transfers energy to the recharging interface circuit acoustically.

11. The defibrillator assembly of claim 1, wherein the external charging circuit transfers energy to the recharging interface circuit magnetically.

12. The defibrillator assembly of claim 1, wherein the defibrillator housing is portable.

13. The defibrillator assembly of claim 1, wherein the defibrillator housing is an automated external defibrillator.

* * * * *

UNITED STATES PATENT AND TRADEMARK OFFICE
CERTIFICATE OF CORRECTION

PATENT NO. : 7,570,994 B2  
APPLICATION NO. : 10/423805  
DATED : August 4, 2009  
INVENTOR(S) : Tamura et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 690 days.

Signed and Sealed this

Seventh Day of September, 2010

David J. Kappos  
*Director of the United States Patent and Trademark Office*